United States Patent [19]

Takisawa et al.

[11] 4,337,370

[45] Jun. 29, 1982

[54] PROCESS FOR THE PREPARATION OF RESORCINOL DERIVATIVES

[75] Inventors: Yukihisa Takisawa, Ibaraki; Shinichi Hasegawa, Otsu, both of Japan

[73] Assignee: Sumitomo Chemical Company, Limited, Osaka, Japan

[21] Appl. No.: 201,746

[22] Filed: Oct. 29, 1980

[30] Foreign Application Priority Data

Nov. 8, 1979 [JP] Japan .............................. 54-145060
Dec. 10, 1979 [JP] Japan .............................. 54-160180

[51] Int. Cl.³ ...................... C07C 37/11; C07C 39/08
[52] U.S. Cl. .................................. 568/766; 568/763; 568/784
[58] Field of Search ............... 568/766, 763, 780, 784, 568/785

[56] References Cited

U.S. PATENT DOCUMENTS

| | | | |
|---|---|---|---|
| 2,439,421 | 4/1949 | Erickson | 568/766 |
| 2,470,902 | 5/1949 | Rosenwald | 568/790 |
| 2,544,818 | 3/1951 | Axe | 568/766 |
| 2,605,252 | 7/1952 | Kitchen | 568/780 |
| 3,360,573 | 12/1967 | Walts et al. | 568/794 |
| 3,919,333 | 11/1975 | Wollensak | 568/766 |
| 4,160,113 | 7/1979 | Muller et al. | 568/772 |
| 4,174,460 | 11/1979 | Seifert et al. | 568/768 |
| 4,260,832 | 4/1981 | Parker et al. | 568/790 |

FOREIGN PATENT DOCUMENTS

| | | | |
|---|---|---|---|
| 216601 | 8/1958 | Australia | 568/766 |
| 473075 | 7/1969 | Switzerland | 568/763 |

OTHER PUBLICATIONS

Flaig et al., "Chemical Abstracts" vol. 52 (19) pp. 1760f, 1759i.

*Primary Examiner*—Werren B. Lone
*Attorney, Agent, or Firm*—Stevens, Davis, Miller & Mosher

[57] ABSTRACT

2-Substituted-4,6-di-t-butylresorcinol represented by the general formula:

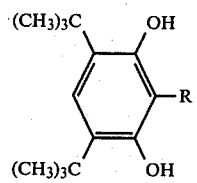

wherein R represents a straight or branched alkyl group having 1 to 20 carbon atoms, a straight or branched alkenyl group having 2 to 20 carbon atoms and at least one double bond, or an aralkyl group, but the tertiary carbon atom of R is free from direct bonding to the benzene nucleus, is prepared by allowing 4,6-di-t-butylresorcinol to react with a halogen compound represented by the general formula:

RX wherein R has the same meaning as defined above, and X represents a halogen atom, excluding the X bonded to the tertiary carbon of R, in an aqueous alkali solution. By further debutylization of the 2-substituted-4,6-t-butylresorcinol, 2-substituted resorcinol represented by the general formula:

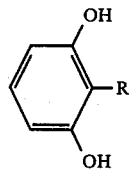

wherein R has the same meaning as defined above, but the tertiary carbon of R is free from direct bonding to the benzene nucleus, is prepared.

6 Claims, No Drawings

PROCESS FOR THE PREPARATION OF RESORCINOL DERIVATIVES

This invention relates to resorcinol derivatives and a process for the preparation thereof, and more particularly to resorcinol derivatives represented by the general formula (I):

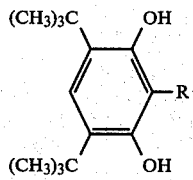

wherein R represents a straight or branched alkyl group having 1 to 20 carbon atoms, a straight or branched alkenyl group having 2 to 20 carbon atoms and at least one double bond, or an aralkyl group, but the tertiary carbon of R is free from direct bonding to the benzene nucleus, and a process for the preparation thereof, and a process for the preparation of resorcinol derivatives represented by the general formula (II):

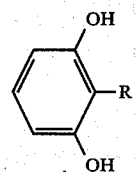

wherein R has the same meaning as defined above, by debutylizing the compound represented by the general formula (I).

Heretofore, alkylation, alkenylation or aralkylation of aromatic compounds in the presence of a Friedel-Craft's type catalyst under an action of an alkyl halide, an alkenyl halide or an aralkyl halide has been regarded as the most popular process. However, when 2-position of 4,6-di-t-butylresorcinol is alkylated, alkenylated or aralkylated according to the above-mentioned process, debutylization reaction occurs, and the desired 2-alkyl-4,6-di-t-butylresorcinol, 2-alkenyl-4,6-di-t-butylresorcinol or 2-aralkyl-4,6-di-t-butylresorcinol is very difficult to obtain. Thus, the compounds represented by the general formula (I) themselves are not known.

The 2-substituted resorcinols represented by the general formula (II) are known as useful raw materials for deriving medicaments, agricultural chemicals, dyes, pigments, photographic reagents, etc. and processes for the preparation thereof have been extensively studied, but any process for preparing the 2-substituted resorcinols in a high yield in an industrially advantageous manner has not been found yet.

For example, when 2-position of resorcinol is substituted according to the ordinary process using a Friedel-Craft's reaction, etc., substitution takes place preferentially at the 4-position or 4- and 6-positions, and only the desired 2-substituted compound cannot be obtained in a good yield. Thus, attempts to increase the selectivity to the 2-position have been made by introducing nitro groups, carboxyl groups, etc. provisionally into the 4-position or 4- and 6-positions. For example, it is known that methyl ester of β-resorcylic acid is at first obtained, and then 2-substituted resorcinol is obtained therefrom through Gattermann reaction, Clemmensen reduction, etc. [J. Chem. Soc., (1938) 1828–1832], but the process involves so many reaction steps that it is complicated. The yield is not so high, either.

Another process is available, which comprises synthesizing cyclohexane-1,3-dione by hydrogenation of resorcinol, as shown in, for example, Org. Syn. Coll. Vol. 5, 743–746, alkylating the cyclohexane-1,3-dione, followed by aromatization thereof, producing 2-substituted resorcinol, for example, as shown in Tetrahedron, Vol. 29, 3857–3859 (1973). However, the process requires a pressurized system at the hydrogenation, and further requires expensive special chemicals such as N-chlorosuccinimide or N,N-dimethyl formamide (DMF). Thus, the process is not industrially advantageous owing to these drawbacks.

On the other hand, in a process of introducing t-butyl groups as a mask into the 4- and 6-positions, debutylization reaction takes place during the reaction of 4,6-di-t-butylresorcinol with an alkyl halide or an aralkyl halide, if the reaction is conducted according to the ordinary method such as Friedel-Craft's reaction, and consequently the desired 2-substituted resorcinol is hardly obtained.

Under these situations, the present inventors have made extensive studies of solving these problems and processes for industrially advantageously preparing resorcinol derivatives represented by the general formula (I) and the general formula (II), and have found that 2-substituted-4,6-di-t-butylresorcinol can be obtained in a good yield by allowing 4,6-di-t-butylresorcinol to react with an alkyl halide, an alkenyl halide or an aralkyl halide in an aqueous alkali solution, thereby inhibiting occurrence of debutylization reaction, and further that 2-substituted-resorcinol can be obtained in a good yield by debutylizing the resulting 2-substituted-4,6-di-t-butylresorcinol, and have established the present invention. 2-Substituted-4,6-di-t-butylresorcinol can be used not only as an intermediate for 2-substituted-resorcinol, but also as a stabilizer by itself.

The present invention provides a process for preparing 2-substituted-4,6-di-t-butylresorcinol represented by the aforementioned general formula (I), which comprises allowing 4,6-di-t-butylresorcinol to react with a halogen compound represented by the general formula (III):

$$RX \qquad (III)$$

wherein R represents a straight or branched alkyl groups having 1 to 20 carbon atoms, a straight or branched alkenyl group having 2 to 20 carbon atoms and at least one double bond, or an aralkyl group, and X represents a halogen atom, excluding the X bonded to the tertiary carbon of R, and also provides a process for preparing 2-substituted resorcinol represented by the aforementioned general formula (II), which comprises debutylizing the compound represented by the aforementioned general formula (I).

The 4,6-di-t-butylresorcinol used in the present invention is a well known compound, and can be readily obtained in a high yield from resorcinol according to the ordinary butylation method.

The halogen compound represented by the general formula (III) includes alkyl halides such as methyl bromide, methyl iodide, methyl chloride, ethyl bromide, ethyl iodide, ethyl chloride, propyl chloride, propyl bromide, propyl iodide, isopropyl chloride, isopropyl bromide, isopropyl iodide, butyl bromide, butyl iodide, pentyl bromide, pentyl chloride, octyl bromide, octyl chloride, dodecyl chloride, dodecyl bromide, eicosyl chloride, eicosyl bromide, etc.; alkenyl halides such as alkyl chloride, allyl bromide, isopropenyl chloride, isopropenyl bromide, 1-propenyl chloride, 1-propenyl bromide, etc.; aralkyl halides such as benzyl chloride, benzyl bromide, etc.

As the alkali compound for the aqueous alkali solution to be used in the present invention, at least one of lithium hydroxide, sodium hydroxide and potassium hydroxide is particularly preferably used. The alkali compound is used in a ratio by mole thereof to 4,6-di-t-butylresorcinol of usually at least 1, practically desirably 1.05–5. The concentration of the aqueous alkali solution is not particularly restricted, but preferably is 10 to 20% by weight.

In the reaction, it is desirable from the viewpoint of an increase in yield to use a solvent, which is inert to the reaction system and immiscible with water, if required. The solvent includes, for example, aromatic and aliphatic hydrocarbons, ethers, etc. such as benzene, toluene, xylene, ethylbenzene, ligroin, n-hexane, cyclohexane, decahydronaphthalene, ethylether, isopropylether, etc. The amount of the solvent is not particularly restricted, but preferably is not more than 5 parts by weight per part by weight of 4,6-di-t-butylresorcinol in view of the decrease in reaction rate, volume efficiency, etc. owing to the excess use.

The amount of the halogen compound represented by the general formula (III) must be theoretically one part by mole per part by mole of 4,6-di-t-butylresorcinol, but usually a little excess over one part by mole, preferably 1.05 to 1.5 parts by mole, of the halogen compound is used per part by mole of 4,6-di-t-butylresorcinol.

Reaction temperature and reaction time depend upon the reactivity of the compound represented by the general formula (III) and also upon other conditions, but usually the reaction temperature is in a range of 40° to 90° C., and the reaction time is in a range of 30 minutes to 24 hours. Generally the reaction time tends to be prolonged with increasing chain length of the compound represented by the general formula (III).

Novel compounds represented by the general formula (I) are synthesized by the aforementioned reaction, and separation and recovery of the desired compound from the reaction solution are carried out by separating the reaction solution into an organic layer and an aqueous layer according to the ordinary method, and isolating the desired compound from the organic layer according to the ordinary procedure such as by recrystallization, etc.

The resulting compound represented by the general formula (I) itself can be used as a stabilizer, etc., but 2-substituted resorcinol represented by the general formula (II) can be readily obtained by debutylizing the compound represented by the general formula (I).

The debutylization reaction is not particularly restricted, and for example, the ordinary procedure using aluminum chloride, hydrogen fluoride, concentrated sulfuric acid, etc. as a catalyst, as shown in J. F. W. Mcomie: Protective Groups in Organic Chemistry, 23–25, is applicable to the debutylization reaction easily in a high yield.

The present invention will be described in detail below, referring to Examples.

EXAMPLE 1

Into a four-necked flask with a capacity of 200 ml, provided with a stirrer, a reflux condenser, a thermometer, and a dropping funnel were charged 22.2 g of 4,6-di-t-butylresorcinol, 66.7 g of an aqueous 12 wt.% sodium hydroxide solution and 50 g of toluene, followed by heating and stirring at 70° C. Then, 15.6 g of methyl iodide was added thereto dropwise over a period of 60 minutes, and the flask was kept at 70° C. for two hours. Then, the reaction solution was neutralized with hydrochloric acid, and left standing to separate the reaction solution into an aqueous layer and an organic layer. The aqueous layer was extracted with ethylether, and the extract ether layer was joined into the above-mentioned organic layer. The solvent was then distilled off from the organic layer, which was then recrystallized from ligroin, whereby 16.7 g of white crystal of 2-methyl-4,6-di-t-butylresorcinol was obtained (m.p. 117°–119° C.; yield 70.7%).

Elemental analysis:

|  | C(%) | H(%) | O(%) |
|---|---|---|---|
| Calculated (as $C_{15}H_{24}O_2$) | 76.2 | 10.2 | 13.5 |
| Found | 76.2 | 10.6 | 13.2 |

Mass spectrography $M^+=236$.

NMR (CDCl$_3$, internal reference TMS, $\delta_{ppm}$, 60 MHz): 7.02 (s, 1H, 5—$\underline{H}$); 4.65 (broad S, 2H, 1—O$\underline{H}$ and 3—O$\underline{H}$); 2.03 (S, 3H, 2—C$\underline{H_3}$); 1.33 (S, 18H, —C$\underline{H_3}$ of t-butyl).

EXAMPLES 2–7

Compounds of the present invention were prepared under reaction conditions shown in Table in the same manner as in Example 1.

Substituent R in Table corresponds to the substituent R of the following structural formula:

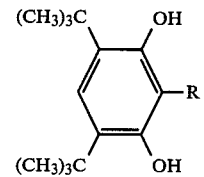

TABLE

| Ex. | Reagent(*1) | Reaction condition | | | | | |
|---|---|---|---|---|---|---|---|
| | | Aq. alkali soln | Solvent | Reaction temp. (°C.) | Heating time (hrs) | Recrystallization solvent | |
| 2 | Ethyl bromide 14.2 g | 20% KOH 70.1 g | Isopropyl ether 30 g | 65 | 3 | Ligroin | |
| 3 | Isopropyl bromide 17.2 g | 15% NaOH 80.0 g | n-hexane 30 g | 70 | 3 | Petroleum ether | |
| 4 | Propyl bromide | 15% KOH | Toluene | 75 | 4 | Petroleum ether | |

TABLE-continued

| | | | | | | |
|---|---|---|---|---|---|---|
| 5 | 14.8 g Allyl bromide 14.5 g | 112.2 g 10% LiOH 35.9 g | 30 g — | 65 | 2 | Petroleum ether |
| 6 | Lauryl bromide 29.9 g | 15% NaOH 106.2 g | Toluene 30 g | 75 | 15 | (Simple distillation) |
| 7 | Benzyl bromide 13.9 g | 15% NaOH 40 g | Toluene 30 g | 70 | 2 | Ligroin |

(*1)Halogen compound and its amount on the basis of 22.2 g of 4,6-di-t-butylresorcinol.

| | | Desired compound | | |
|---|---|---|---|---|
| Ex. | R | Amount produced (yield) | Color mp, (b.p.) | Mass spectrographic analysis M+ |
| 2 | Ethyl | 18.8 g (75.1%) | White crystal 112°–114° C. | 250 |
| 3 | Isopropyl | 20.8 g (78.7%) | White crystal 103°–106° C. | 264 |
| 4 | Propyl | 19.4 g (73.4%) | White crystal 67°–70° C. | 264 |
| 5 | Allyl | 19.4 g (73.9%) | White crystal 59°–60° C. | 262 |
| 6 | Dodecyl | 30.4 g (77.8%) | Yellow liquid (190° C./1 mmHg) | 390 |
| 7 | Benzyl | 23.6 g (75.6%) | White crystal 120°–121° C. | 312 |

NMR data of the desired compounds obtained in the above-mentioned examples are given below:

EXAMPLE 2

(CDCl$_3$, internal reference TMS, $\delta_{ppm}$, 60 MHz):
7.02 (S, 1H, 5—H); 4.73 (broad S, 2H, 1—OH and 3—OH); 2.60 (q, 2H, 2—CH$_2$—CH$_3$); 1.36 (s, 18H, —CH$_3$ of t-butyl); 1.16 (t, 3H, 2—CH$_2$—CH$_3$).

EXAMPLE 3

(CDCl$_3$, internal reference TMS, $\delta_{ppm}$, 90 MHz):
7.04 (s, 1H, 5—H); 4.90 (broad S, 2H, 1—OH and 3—OH); 3.51 (Sptet, 1H, 2—CH(CH$_3$)CH$_3$); 1.44 (d, 1.44+1.42 total 24H, 2—CH(CH$_3$)CH$_3$); 1.42 (s, 1.44+1.42 total 24H, —CH$_3$ of t-butyl).

EXAMPLE 4

(CDCl$_3$, internal reference TMS, $\delta_{ppm}$, 90 MHz):
7.06 (s, 1H, 5—H); 4.79 (broad S, 2H, 1—OH and 3—OH); 2.61 (t, 2H, 2—CH$_2$—CH$_2$CH$_3$); 1.67 (m, 2H, 2—CH$_2$—CH$_2$—CH$_3$); 1.41 (s, 18H, —CH$_3$ of t-butyl); 1.06 (t, 3H, 2—CH$_2$CH$_2$—CH$_3$).

EXAMPLE 5

(CCl$_4$, internal reference TMS, $\delta_{ppm}$, 90 MHz):
7.00 (s, 1H, 5—H); 5.95 (complex m, 1H, 2—CH$_2$—CH=CH$_a$H$_b$); 5.22 (m, 1H, —CH$_2$—CH=CH$_a$H$_b$); 5.09 (m, 1H, —CH$_2$—CH=CH$_a$H$_b$); 4.75 (broad S, 2H, 1—OH and 3—OH); 3.44 (m, 2H, 2—CH$_2$—CH=CH$_a$H$_b$); 1.40 (s, 18H, —CH$_3$ of t-butyl).

EXAMPLE 6

(CDCl$_3$, internal reference TMS, $\delta_{ppm}$, 90 MHz):
7.07 (s, 1H, 5—H); 4.75 (broad S, 2H, 1—OH and 3—OH); 2.60 (t, 2H, 2—CH$_2$—(CH$_2$)$_{10}$—CH$_3$); 1.41 (s, 20H, 2—CH$_2$—(CH$_2$)$_{10}$—CH$_3$); 1.30 (s, 18H, —CH$_3$ of t-butyl); 0.90 (t, 3H, 2—(CH$_2$)$_{11}$—CH$_3$).

EXAMPLE 7

(CDCl$_3$, internal reference TMS, $\delta_{ppm}$, 90 MHz):
7.15 (m, 5H, benzene proton of benzyl); 6.99 (S, 1H, 5—H); 4.52 (broad S, 2H, 1—OH and 3—OH); 3.99

(S, 2H, 2-CH$_2$— 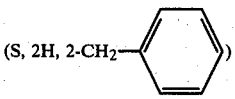 )

1.39 (S, 18H, —CH$_3$ of t-butyl).

EXAMPLE 8

23.6 g of 2-methyl-4,6-di-t-butylresorcinol obtained in the same manner as in Example 1, 30.0 g of nitrobenzene and 0.12 g of concentrated sulfuric acid were charged into a four-necked flask with a capacity of 100 ml, provided with a stirrer, a reflux condenser and a thermometer, and heated to 200° C. and kept at that temperature for one hour, while generated gas was led to a gas absorber tube and absorbed into concentrated sulfuric acid. Then, nitrobenzene was distilled off by reduced-pressure distillation, and then 9.9 g of 2-methylresorcinol as a distillate was obtained (138° C./10 mmHg, m.p. 118°–121° C. Yield 79.8%)

EXAMPLE 9

72.8 g of crude crystal of 2-ethyl-4,6-di-t-butylresorcinol obtained in the same manner as in Example 2 was melted at 115° C. with stirring, admixed with 0.35 g of concentrated surfuric acid, and gradually heated and kept at 230° C. for one hour, while generated gas was led to a gas absorber tube, and absorbed into concentrated sulfuric acid. After the end of reaction, 50 g of water and 50 g of toluene were added to the reaction solution, thoroughly shaken, and then left standing to separate the reaction solution into an aqueous layer and an oil layer. The oil layer was extracted twice with 30 g of water, and the extract aqueous layer was joined into the separated aqueous layer. After water was distilled off from the aqueous layer, the residue was distilled under a reduced pressure, whereby 27.1 g of 2-ethylresorcinol was obtained (145° C./10 mmHg; m.p. 98°–100° C.).

EXAMPLE 10

69.2 g of 2-isopropyl-4,6-di-t-butylresorcinol obtained in the same manner as in Example 3 was dissolved in 80.0 g of nitrobenzene with stirring, then admixed with 0.19 g of concentrated sulfuric acid, gradually heated, and kept under nitrobenzene reflux (200°–210° C.) for one hour, while generated gas was led to a gas absorber tube, and absorbed into concentrated sulfuric acid. After the end of reaction, nitrobenzene was distilled off from the reaction solution by reduced-pressure distillation, and the residue was further distilled, whereby 30.9 g of 2-isopropylresorcinol was obtained (144°–150° C./10 mmHg; m.p. 79°–82° C.).

EXAMPLE 11

108.0 g of 2-dodecyl-4,6-di-t-butylresorcinol obtained in the same manner as in Example 6 was admixed with 0.28 g of concentrated sulfuric acid with stirring, gradually heated and kept at 250° C. for one hour, while generated gas was led to a gas absorber tube, and absorbed into concentrated sulfuric acid. After the end of reaction, 172.8 g of crystal of 2-dodecylresorcinol was obtained by recrystallization from petroleum ether (m.p. 75°–77° C.).

EXAMPLE 12

75.2 g of 4,6-di-t-butylresorcinol was added to 87.8 g of an aqueous 15.9 wt.% sodium hydroxide solution and 84.7 g of toluene, and heated, dissolved, then admixed dropwise with 40.5 g of benzyl chloride at the same temperature over a period of 30 minutes, and kept at that temperature for further 3 hours with stirring. After the end of reaction, the resulting reaction solution was separated into an aqueous layer and an oil layer. The oil layer was washed twice with 116.7 g of an aqueous 5 wt.% sodium hydroxide solution, and then further washed several times with a small amount of water. The solvent was distilled off from the oil layer, whereby 81.8 g of crude crystal of 2-benzyl-4,6-di-t-butylresorcinol was obtained. The 2-benzyl-4,6-di-t-butylresorcinol was dissolved in 94.3 g of nitrobenzene with stirring, then admixed with 0.41 g of concentrated sulfuric acid, gradually heated, and kept under nitrobenzene reflux (200°–210° C.) for one hour, while generated gas was led to a gas absorber tube and absorbed into concentrated sulfuric acid. Then, nitrobenzene was distilled off therefrom by reduced-pressure distillation, and then 37.3 g of crystal of 2-benzylresorcinol was obtained by recrystallization from benzene (m.p.: 80°–82° C.).

COMPARATIVE EXAMPLE

Into a four-necked flask with a capacity of 100 ml, provided with a stirrer, a reflux condenser, a thermometer, and a dropping funnel were charged 6.7 g of aluminum chloride and 20.0 g of nitrobenzene, and the flask was kept at 20° C. Then, 11.1 g of 4,6-di-t-butylresorcinol dissolved in 11.1 g of nitrobenzene was dropwise added thereto over a period of 30 minutes, and the solution was stirred at the same temperature for two hours. Then, the solution was admixed with dilute hydrochloric acid and chloroform, left standing, and separated into an aqueous layer and an oil layer. The aqueous layer was extracted with methylisobutylketone, and the extract oil layer was joined into the oil layer. The oil layer was analyzed by gas chromatography. It was found that 8.0 g of 4,6-di-t-butylresorcinol, 2.2 g of 4-t-butylresorcinol and 0.06 g of resorcinol were contained, and the desired 2-methyl-4,6-di-t-butylresorcinol was not contained.

What is claimed is:

1. A process for preparing 2-substituted-4,6-di-t-butylresorcinol represented by the general formula:

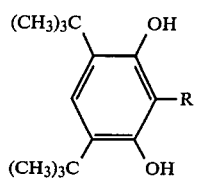

wherein R represents a straight or branched alkyl group having 1 to 20 carbon atoms, a straight or branched alkenyl group having 2 to 20 carbon atoms and at least one double bond, or an aralkyl group, but the tertiary carbon of R is free from direct bonding to the nucleus which comprises allowing 4,6-di-t-butylresorcinol to react with a halogen compound represented by the general formula:

RX wherein R has the same meaning as defined above and X represents a halogen atom, excluding the X bonded to the tertiary carbon of R, in an aqueous alkali solution.

2. A process for producing 2-substituted resorcinol represented by the general formula:

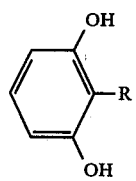

wherein R represents a straight or branched alkyl group having 1 to 20 carbon atoms, a straight or branched alkenyl group having 2 to 20 carbon atoms and at least one double bond, or an aralkyl group, but the tertiary carbon atom of R is free from direct bonding to the benzene nucleus, which comprises allowing 4,6-di-t-butylresorcinol to react with a halogen compound represented by the general formula:

RX wherein R has the same meaning as defined above, and X represents a halogen atom, excluding the X bonded to the tertiary carbon of R, in an aqueous alkali solution, thereby obtaining 2-substituted-4,6-di-t-butylresorcinol represented by the general formula:

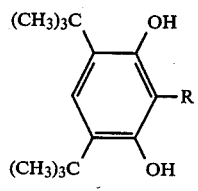

wherein R has the same meaning as defined above, but the tertiary carbon of R is free from direct bonding to the benzene nucleus, and debutylizing the 2-substituted-4,6-t-butylresorcinol.

3. A process according to claim 1 or 2, wherein the alkali is at least one of lithium hydroxide, sodium hydroxide, and potassium hydroxide.

4. A process according to claim 1 or 2, wherein an amount of alkali of the aqueous alkali solution is 1.05–5 parts by mole per part by mole of 4,6-di-t-butylresorcinol.

5. A process according to claim 1 or 2, wherein the aqueous alkali solution has a concentration of 10–20% by weight.

6. A process according to claim 1 or 2, wherein an amount of the halogen compound is 1.05–1.5 parts by mole per part by mole of 4,6-di-t-butylresorcinol.

* * * * *